(12) United States Patent
De Hoogh et al.

(10) Patent No.: US 12,424,313 B2
(45) Date of Patent: Sep. 23, 2025

(54) REAL-TIME PROXIMITY-BASED DEVICE OVERVIEW DASHBOARD

(71) Applicant: KONINKLIJKE PHILIPS N.V., Eindhoven (NL)

(72) Inventors: Sebastiaan Jacobus Antonius De Hoogh, Oosterhout (NL); Sauvik Bhattacharya, Eindhoven (NL); Falk Uhlemann, Norderstedt (DE); Mauro Barbieri, Eindhoven (NL); Tiblets Zeray Demewez, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 171 days.

(21) Appl. No.: 18/231,271

(22) Filed: Aug. 8, 2023

(65) Prior Publication Data
US 2024/0062888 A1    Feb. 22, 2024

Related U.S. Application Data

(60) Provisional application No. 63/371,642, filed on Aug. 17, 2022.

(51) Int. Cl.
*G16H 40/40*    (2018.01)

(52) U.S. Cl.
CPC .................................. *G16H 40/40* (2018.01)

(58) Field of Classification Search
CPC ......... G16H 40/40; G16H 40/67; G16H 40/20
See application file for complete search history.

(56) References Cited

U.S. PATENT DOCUMENTS

| | | | |
|---|---|---|---|
| 2005/0035862 A1* | 2/2005 | Wildman | G08B 21/0446 340/572.1 |
| 2014/0201266 A1 | 7/2014 | Jackson | |
| 2016/0007937 A1 | 1/2016 | Georgiev | |
| 2021/0074417 A1* | 3/2021 | Pierson | H04L 67/52 |

FOREIGN PATENT DOCUMENTS

WO    WO-2008063936 A2 *    5/2008    ........... G06F 19/327

OTHER PUBLICATIONS

Ross, Ian. "Containing infection through GIS; pilot program planned for Sault hospital." Northern Ontario Business: 29.2: 15(2). Laurentian Business Publishing, Inc. (Dec. 2008) (Year: 2008).*
Wikipedia, Indoor positioning system https://en.wikipedia.org/wiki/Indoor_positioning_system.
Wikipedia, Real-time locating system https://en.wikipedia.org/wiki/Real-time_locating_system.
Wikipedia, Approximate string matching https://en.wikipedia.org/wiki/Approximate_string_matching.
(Continued)

*Primary Examiner* — Linh Giang Le

(57) ABSTRACT

In a method of locating medical equipment to be serviced, a map of a medical facility is accessed using an electronic processing device. The map includes a plurality of medical equipment each having a tag indicative of a location thereof. A user input is received which is indicative of a selection of a medical equipment of the plurality of medical equipment. A list of service actions to be performed for the selected medical equipment is displayed on a display device of the electronic processing device.

20 Claims, 3 Drawing Sheets

(56) References Cited

OTHER PUBLICATIONS

Here, Indoor Positioning https://www.here.com/platform/tracking-positioning-solutions/indoor-positioning-systems.
Securitas Healthcare, Healthcare RTLS Systems for Hospitals https://www.stanleyhealthcare.com/hospital-clinics/rtls.
Centrak, RTLS for Hospitals: Improving Facilities for Patients and Staff, https://centrak.com/products/real-time-location-services/.

* cited by examiner

REAL-TIME PROXIMITY-BASED DEVICE OVERVIEW DASHBOARD

CROSS REFERENCE TO RELATED APPLICATIONS

This claims the benefit of U.S. Provisional Patent Application No. 63/371,642 filed Aug. 17, 2022. This application is hereby incorporated by reference herein.

FIELD

The following relates generally to the tracking arts, medical equipment tracking arts, medical device maintenance arts, real-time location system (RTLS) arts, and related arts.

BACKGROUND

Medical devices are remotely monitored to proactively prevent medical device malfunction. Typically, when service is required, an alert is generated indicating the service that is needed. The alert together with relevant information and service action is shared with the person who is responsible for maintaining the medical device.

Alerts come in different forms, ranging from critical alerts requiring immediate action to informational alerts aimed at keeping stakeholders regularly aware of the medical device's status. Hence, in large medical centers with several medical devices, keeping track of the alerts in a structured way and taking severity into account is required to keep alerts actionable and avoid flooding service personnel with an overwhelming number of alerts.

Biomedical engineer ("bio-meds") responsible for the operation of the medical devices should be aware of the status of all the medical devices located in in different departments and floors. Hence, whenever a device needs service, a biomed or a service engineer should be able to find all related alerts and service actions corresponding to the device easily. The bio-meds receive enormous amount of information from diagnostic tools in the form of alerts. Unstructured or unfiltered alerts can overwhelm their schedule and prevent them from acting on the most critical ones. Unnecessary time can be spent by biomedical engineers in finding specific alerts from a dashboard, database, or report, and availability of large amounts of unstructured and repeated information in the service history can result in wasted time searching for relevant information. To efficiently plan and schedule service actions, knowledge of the physical locations of the medical devices is also required, so that the biomed can minimize travel time between service tasks on different medical devices.

The following discloses certain improvements to overcome these problems and others.

SUMMARY

In one aspect, a non-transitory computer readable medium stores instructions executable by at least one electronic processor to perform a method of locating medical equipment to be serviced. The method includes: accessing a map of a medical facility using an electronic processing device, the map including a plurality of medical equipment each having a tag indicative of a location thereof; receiving a user input indicative of a selection of a medical equipment of the plurality of medical equipment; and displaying, on a display device of the electronic processing device, a list of service actions to be performed for the selected medical equipment.

In another aspect, in a non-transitory computer readable medium as set forth in the immediately preceding paragraph, the method further includes: determining priorities of the medical equipment having queued service actions based on the queued service actions for each medical equipment; and on the map, displaying indicators representing the determined priorities for the medical equipment having queued service actions. In some embodiments, the indicators are determined further based on distances of the medical equipment from a location of a user.

In another aspect, a non-transitory computer readable medium stores instructions executable by at least one electronic processor to perform a method of locating medical equipment to be serviced. The method includes: accessing a map of a medical facility using an electronic processing device, the map including queued service actions for the medical equipment, the queued service actions indicated by indicators; receiving a user input indicative of a selection of one of the indicators; and displaying information related to the service action corresponding to the selected indicator.

In another aspect, an apparatus includes: a real-time locating service (RTLS) dispersed throughout a medical facility, the RTLS configured to determine locations of medical equipment in the medical facility; and an electronic processing device programmed to: access a map of the medical facility, the map including queued service actions for the medical equipment, the queued service actions indicated by an indicator; receive a user input indicative of a selection of a medical equipment of the plurality of medical equipment; and display, on a display device of the electronic processing device, a list of service actions to be performed for the selected medical equipment.

One advantage resides in displaying a list of alerts with the related positions of the medical devices that need service, along with a position of a biomed scheduled to perform the service.

Another advantage resides in mapping a location between a device to be serviced and the person scheduled to perform the service.

Another advantage resides in allowing a user to zoom in or out on a map to find a medical device to be serviced.

Another advantage resides in providing for the sorting of alerts for medical devices needing servicing based on locations of the devices in a medical facility.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
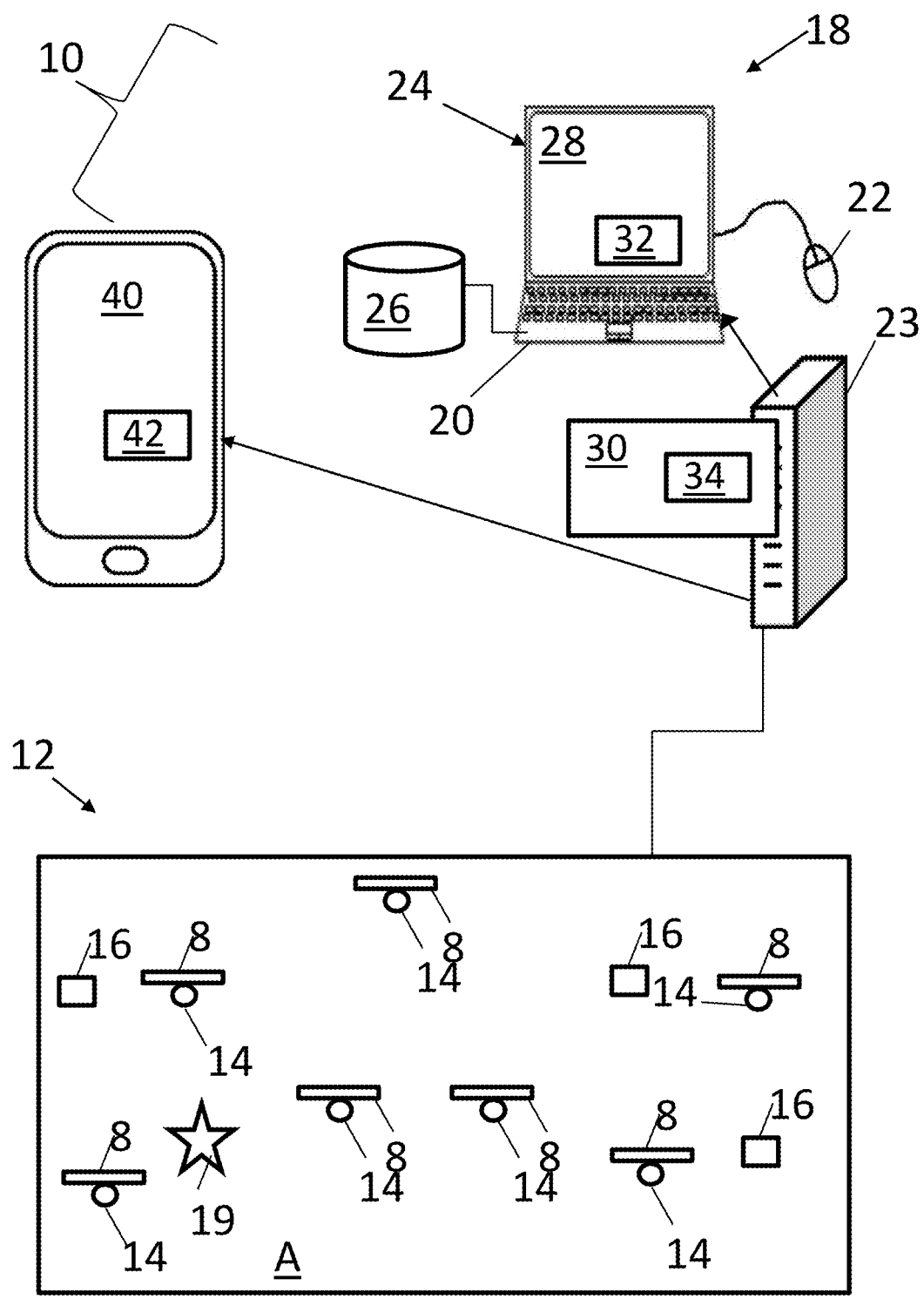
FIG. 1 diagrammatically illustrates an illustrative system for tracking locations of medical equipment in accordance with the present disclosure.

Large hospitals or other large-scale medical service providers may have a large inventory of medical equipment. At any given time, a significant number of these medical devices may need servicing, ranging from preventative maintenance with low severity rating to urgent repairs with high severity rating. Moreover, these pieces of equipment are distributed amongst various medical departments, laboratories, or other diverse locations. Furthermore, some types of medical devices may be portable. Some medical equipment may be unavailable for servicing at any given time (e.g., in use with patients). A biomed or service engineer on call may, therefore, waste significant time simply locating equipment that is currently available for servicing.

The following discloses a navigational system tailored to the task of assisting a biomed or service engineer in locating equipment to be serviced. The system leverages a real-time locating service (RTLS) having an electronic map of the hospital with locations of medical devices marked. Portable medical equipment may be tagged with a radio frequency (RF) locator tag, infrared locator tag, or the like that can be read by the RTLS, so its current location is known to the RTLS. In some RTLS systems, such as the CenTrak system, the tag includes a bar code which can be scanned by a dedicated bar code scanner or a mobile device (i.e., a smartphone). The scanning devices stores the bar code of the tag in a database of or accessible by the RTLS so as to associate the tag with the tagged medical device.

The disclosed system further maintains a database of queued service actions annotated to specific medical devices. In one nonlimiting illustrative embodiment, the queued service actions are alerts with systemAlertUIDs and associated metadata (AlertMetaData), and the medical devices are stored with LocationMetaData. As the systemAlertUIDs may use different notation for identifying the device compared with the LocationMetaData, approximate string matching or other flexible matching can be used to associate alerts to mapped medical devices.

The biomed or service engineer (i.e. "user") uses a mobile device such as a cellular telephone (cellphone) or tablet computer with a navigational system application program ("app") loaded thereon. Upon opening the app, the location of the mobile device (and hence the location of the user) is determined using the RTLS and/or another system such as GPS, Wi-Fi access point triangulation, or so forth. The app presents a map of the local area with queued service actions indicated by flags or other indicators. The user can zoom in or out by a gesture control such as pinching in/out, or by selecting a particular department or other geographical location, and the displayed area of the map is adjusted accordingly. In a variant embodiment, if the user is only qualified to perform a subset of the queued service actions, then only the indicators for that subset are shown. For example, if a particular user is qualified to service magnetic resonance imaging (MRI) scanners, but is not qualified to service computed tomography (CT) scanners, then only alerts for MRI scanners but not for CT scanners will be shown to that user. The service action indicators may be color coded by severity.

By selecting a service indicator on the map, more information about that service action is brought up on a popup window or other dialog. Other interactions might include showing a list of nearby service actions with some details about them.

In a variant embodiment, the disclosed system can monitor medical devices that may be unavailable for servicing (e.g. in-use). If the hospital maintains a content management system (CMS) that stores scheduling information, then the CMS can be accessed to determine availability of various medical devices for the purpose of servicing, and the service action indicators for any unavailable devices can be grayed out or removed entirely from the map. Selection of a grayed-out service action indicator might bring up schedule information to indicate when the device will become available for servicing.

In another contemplated variant, if the user is seeking to immediately service a specific alert, then the user can enter the systemAlertUID or other alert identifier, and app identifies the corresponding medical device and its location, and the displayed map area is shifted and/or zoomed in or out to show the current location of that medical device. Optionally, an area of the map may be displayed that includes both the location of the user and the location of the medical device, and a route for the user to travel to reach the medical device may be superimposed on the map.

With reference to FIG. 1, an illustrative tracking system 10 for optimizing quality control of tracking data is shown. The tracking system 10 includes a real-time locating system (RTLS) 12 configured to perform tracking of persons (i.e., patients or medical personnel) or items (medical devices such as IV pumps, beds, equipment, and so forth) in a building or monitored area A with tags 14 (e.g., radiofrequency identification (RFID) tags, or IR tags) and corresponding tag localization stations 16 (diagrammatically shown as rectangles in FIG. 1) which are placed at a priori-known fixed locations. In the CenTrak system, for example, the tag localization stations 16 operate as beacons that transmit IR identifier signals which are detected by any tag 14 in proximity to the beacon. The tags 14 output location reports determined from the received beacon signals to radio receivers (called "stars" in the CenTrak system) via radio transmissions to provide the location tracking. In other embodiments, the tag localization stations 16 may be tag readers that read an IR signal emitted by a tag 14 in proximity to the tag reader, so as to provide the location tracking. The localization stations 16 are distributed through the monitored area A and are configured to track locations of the tags 14 in the monitored area, either by operating as beacons as in the CenTrak system, or by reading IR or RF signals emitted by the tags 14. For example, the tags 14 are attached or otherwise secured to one or more nodes 8 (e.g., a patient, a medical professional, a mobile object such as a piece of medical equipment, a zone in the building A, and the like). The tags 14 may be referred to by other terms, e.g. badges, tracking chips, et cetera—the term "tag" as used herein is intended to encompass such alternative nomenclatures. The localization stations 16 are distributed throughout the building A where persons or mobile objects to be tracked may traverse (e.g., in a patient room, in a hallway, at a workstation of a medical professional, and the like). In some examples, the building A can be a two-dimensional area (i.e., a single floor of a hospital) while in other examples, the monitored area can be a three-dimensional area (i.e., multiple floors of a hospital).

The localization stations 16 are configured to establish location data for proximate tags 14, thereby allowing the RTLS to track a corresponding node 8. In one design, a localization station 16 may have an operational range, e.g. five meters, and any tag localized by that localization station 16 is known to be within a five-meter radius of the localization station. In other designs, two or three or more localization stations with overlapping operational ranges may operate in concert to locate a tag more precisely, e.g. using triangulation or the like. In yet other designs, a single localization station may provide directional information using a phased array transducer, a rotating transducer, or so forth. These are merely illustrative examples of RTLS ranging and angulating technologies, and more generally the RTLS 12 may use any suitable tracking technology to provide real time locational information for the tags present in the building A.

The tag localization information may take various forms, e.g. in active tag designs the tag 14 includes an on-board battery-powered microprocessor or microcontroller and associated nontransitory memory (e.g. a FLASH, PROM, or other electronic memory chip) that stores a tag identifier number or the like which the tag 14 transmits to the localization station 16 which is in this embodiment a tag reader 16. In a passive tag design, radio frequency energy transmitted by the localization station 16 to the tag 14 powers the tag to drive it to transmit its tag identifier. In other designs, each tag may transmit at a different frequency and the tag is identified by its response frequency. These are merely illustrative examples of tag identification technologies, and more generally the RTLS 12 may use any suitable tag identification technology to by which the tags 14 and localization stations 16 cooperatively generate real time location reports for the detected/tracked tags. Optionally, the RTLS 12 may be compliant with an industry-defined RTLS standard, e.g. ISO/IEC 24730-1 or a variant thereof.

The system 10 includes an electronic processing device 18, 23 such as a workstation 18 (e.g., a computer, a smart tablet, and so forth), a server computer 23, various combinations thereof, or more generally a computer. The server computer 23 may comprise a plurality of server computers, e.g. interconnected to form a server cluster, cloud computing resource, or so forth, to perform more complex computational tasks. The workstation 18 and/or server 23 includes typical components, such as an electronic processor 20 (e.g., a microprocessor), at least one user input device (e.g., a mouse, a keyboard, a trackball, a device with an embedded screen such as a tablet, a smartphone, a smartwatch, an alternate reality/virtual reality headset or goggles, and/or the like) 22, and a display device 24 (e.g. an LCD display, plasma display, cathode ray tube display, and/or so forth). In some embodiments, the display device 24 can be a separate component from the workstation 18, or may include two or more display devices.

The electronic processor 20 is operatively connected with one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a visualization of a graphical user interface (GUI) 28 for display on the display device 24.

Figure 2:
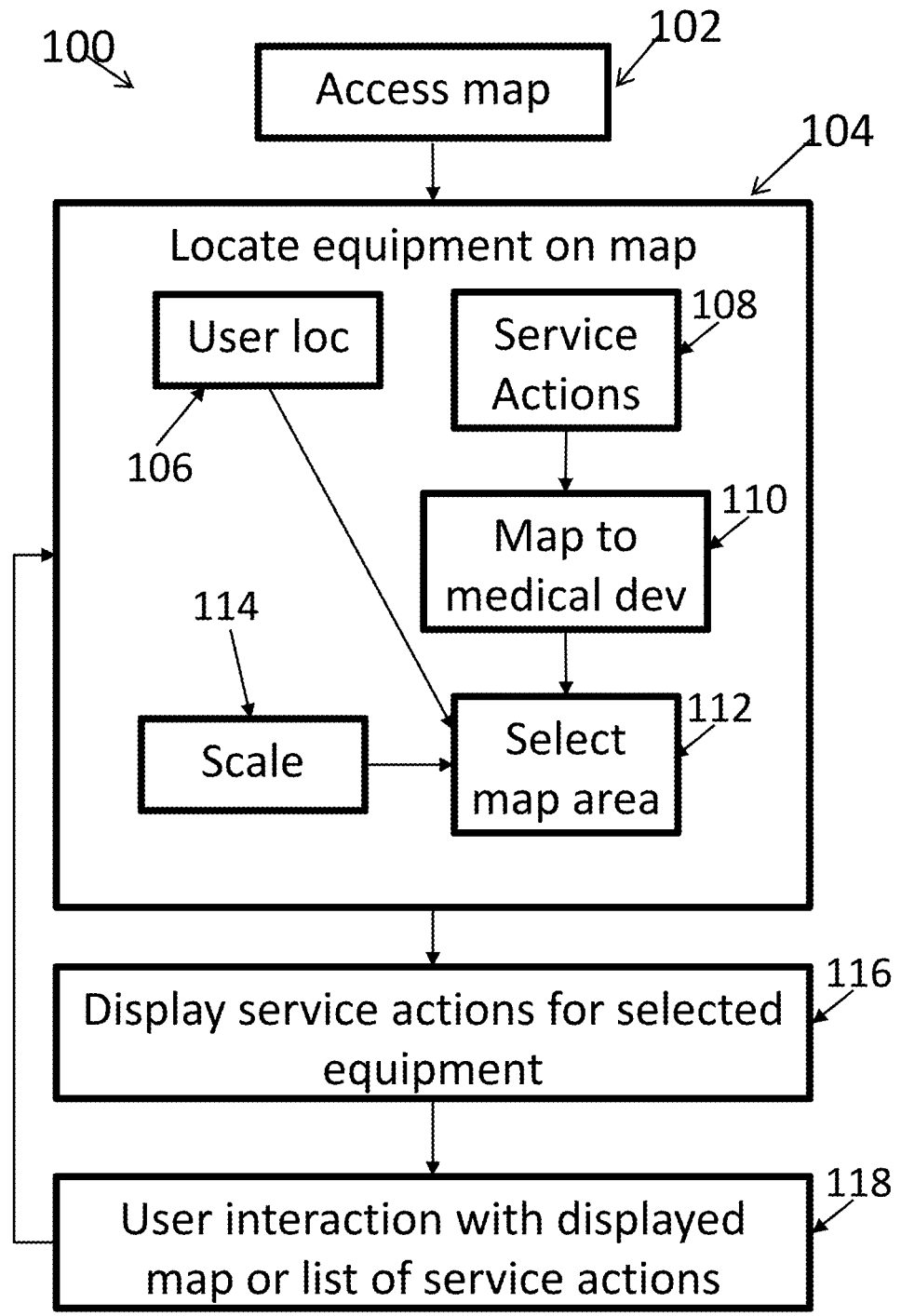
FIG. 2 shows exemplary flow chart operations of the system of FIG. 1.

With reference to FIG. 2, and with continuing reference to FIG. 1, the non-transitory storage media 26 stores instructions which are readable and executable by the electronic processor 20 to perform a method or process 100 of locating medical equipment (i.e., one or more of the nodes 8) to be serviced in the building A. In some examples, the method 100 may be performed at least in part by cloud processing.

At an operation 102, the electronic processing device 18 is configured to access a map 30 of the medical facility A (stored in the server computer 23) and display the map 30 on the display device 24. The map 30 can include a plurality of medical equipment 8 each having a tag 14 indicative of a location thereof. The map 30 can correspond generally to the image of the medical facility A shown in FIG. 1. At an operation 104, medical devices with open service actions are selected to display on the map. In one embodiment of the operation 104, a user input indicative of a selection of a medical equipment 8 of the plurality of medical equipment on the display of the map 30 is received (e.g., via a user input provided by the at least one user input device 22). In another embodiment (which is diagrammatically shown in FIG. 2), the operation 104 automatically selects the medical devices based on the current location 106 of the user (from the RTLS) and the queue of service actions 108. In an operation 110, the service actions 108 are mapped to locations of corresponding medical devices. The alerts typically include the identification of the corresponding medical device and the RTLS provides locations of those medical devices, and thus operation 110 entails one-to-one mapping of systemAlertUID (representing the service action) and systemLocationUID (representing the location of the corresponding medical device). In an operation 112, the map area is chosen, at least initially based on the user location 106 and a map scale 114. At an operation 116, a list 32 of service actions to be performed for the selected medical equipment 8 is displayed on the display device 24, along with a map of the service actions within the map area selected in operation 112.

In an operation 118, a user input (provided by the user via the at least one user input device 22) can be received by the electronic processing device 18. The user input can be an input indicative of a selection of a portion of the map 30 as displayed on the display device 24. For example, the user can change the scale 114 using an operation such as pinch-in on a touch-sensitive display to zoom in (reduce the scale) or a pinch-out operation to zoom out (increase the scale). In another contemplated user interaction, the user may touch a location on the map to re-center the map to that location, or may touch a service action of the list 32 to cause the corresponding marker on the map to highlight. These are merely some nonlimiting contemplated interactions. In response to the interaction of operation 118, flow returns to operation 104 to update the map accordingly. In the repetition of the operation 104, the display of the map 30 is adjusted on the display device 24 by, for example, zooming in or zooming out of a selected portion of the map 30, showing a department or room of the building A on a selected portion of the map 30, and so forth. The process loop 104, 116, 118 can be repeated for each user interaction to provide an interactive map of the open service actions.

In some embodiments, the map 30 includes queued service actions for the medical equipment 8. For example, the queued service actions indicated by an indicator 34 on the display of the map 30. In one example, each item of medical equipment 8 that has at least one queued service action has a corresponding indicator. In another example, the indicator 34 for each item of medical equipment can be color-coded by severity of the queued service action for that medical equipment of highest severity. In another example, the indicators 34 can indicate priorities of corresponding items of medical equipment 8 determined by another prioritization scheme. In this embodiment, the method 100 can include determining qualifications of the user accessing the map 30 using the electronic processing device 18, and showing the indicators 34 for service actions for which the user is qualified to perform.

In another example of the user interaction 118, a user input (provided by the user via the at least one user input device 22) can be received, and be indicative of a selection of one of the indicators 34. Information can then be displayed on the display device 24. The displayed information can include information related to the service action corresponding to the selected indicator 34, information related to service actions corresponding to one or more indicators 34 near the selected indicator 34, and so forth.

In another example, data indicative of queued service actions annotated to specific medical equipment can be retrieved from the server computer 23. The indicators 34 indicative of the queued service actions can then be generated on the map 30. To do so, location data of the medical equipment 8 can be retrieved from the localization stations 16, and the retrieved queued service action data is matched to the location data to generate the indicators 34 as described for operations 108 and 110.

In some embodiments, the location 106 of the user accessing the map 30 using the electronic processing device 18 can be determined using the RTLS 12, or alternatively a global positioning system (GPS) or a Wi-Fi access point triangulation system dispersed throughout the medical facility. A user input indicative of a selection of a medical equipment 8 can be received in the operation 118, and a path between the electronic processing device 18 and the selected medical equipment 8 can be displayed on the display device 24.

In some embodiments, the electronic processing device 18 can determined whether one or more of the medical equipment 8 is unavailable for servicing. To do so, a content management system (CMS) that stores scheduling information for the service actions to determine availability of the medical equipment 8 for servicing. The CMS can be implemented, for example, in the server computer 23. Indicators 34 for unavailable medical equipment (for example, medical equipment currently in use performing medical tasks) can be omitted, shaded, filled in, or otherwise marked, shown partially grayed out, or otherwise modified on the display of the map 30 so that the user recognizes those equipment are currently unavailable for servicing. In some examples, a marked indicator 34 can be selected via the at least one user device 22, and a time at which the medical equipment 8 associated with the marked indicator 34 will be available for servicing can be displayed on the display device 24.

Referring back to FIG. 1, in lieu of the electronic processing device 18, the method 100 can be implemented on a mobile device 40 (e.g., a cellphone, as shown in FIG. 1) operable by the user via a communication link, which typically comprises the Internet possibly augmented by local area networks. For example, the user can log-in into a mobile application program ("app") 42 which is provided as a component of the apparatus 10, and is loaded on, and executable on, the mobile device 40 of the patient (e.g., an illustrative cellular telephone 40, or a tablet computer, personal data assistant or PDA, and/or so forth) to receive the map 30. The app 42 may be downloaded to the mobile device 40 from an app store (such as Google Play or Apple Store) accessed via a Wi-Fi, cellular, or other wireless communication network. In a suitable embodiment, the app 42 is represented on the home screen or applications screen of the mobile device 40 as an app icon (i.e., a small square, round, or other compact graphical element representing the app) and the user launches (i.e., initiates running of) an instance of the app 42 on the device 40 by touching the icon on a (touch-sensitive) screen of the mobile device 40. In another example, in lieu of the app 42, the map 30 can be sent to the mobile device 40 in any suitable format, such as a pre-recorded voice communication, an automated phone call, an email, a short message service (SMS) message, (i.e., a text message), and so forth.

Figure 3:
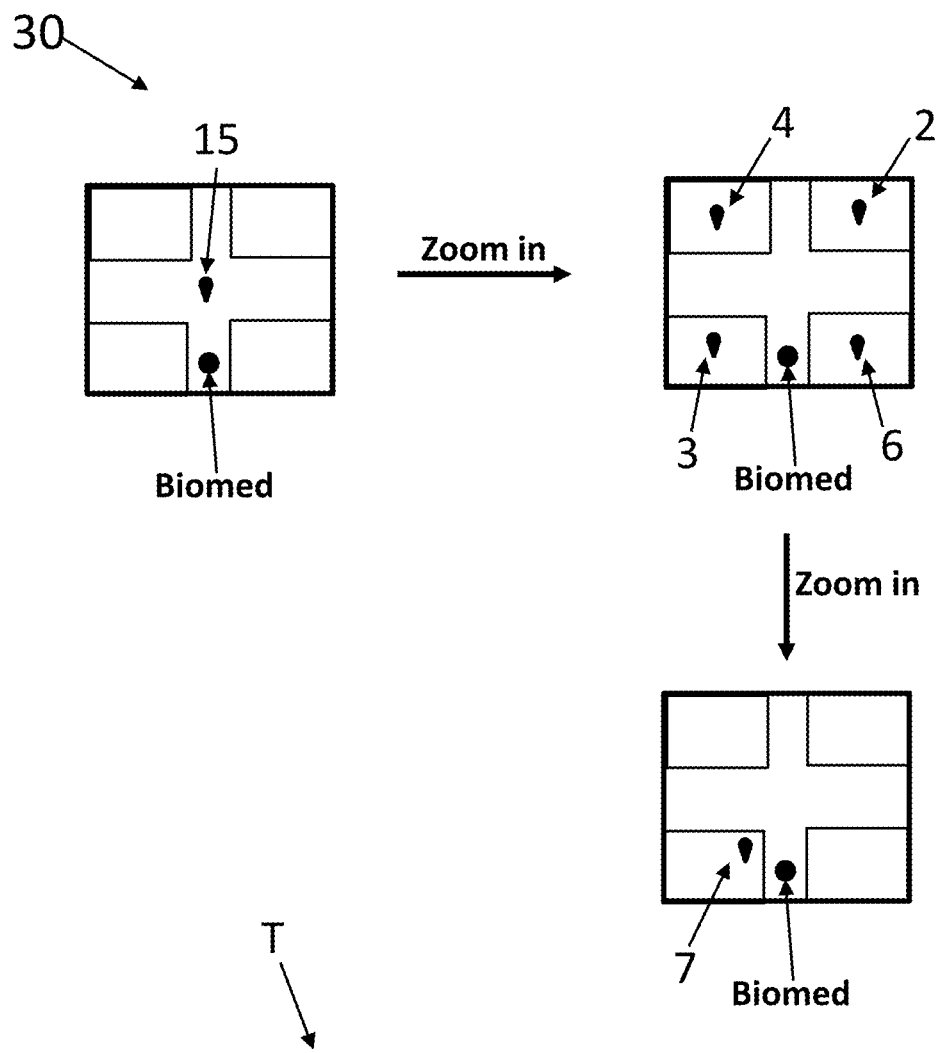
FIG. 3 shows an example map used by the system of FIG. 1.

FIG. 3 shows an embodiment of the app 42 on the mobile device 40. The app 42 displays an example of alert view provided by the dashboard for in a medical center where there are various devices are distributed in a floor. The numbers correspond to location and range settings. In this example, setting 15 covers a whole floor, while settings 2,3,4,6 cover a single room. Finally, setting 7 covers a small area in a room. The table T illustrates an example alerting presentation, i.e. the list 32 of service actions to be performed.

EXAMPLE

The following example describes the system 10 and the method 100 in more detail. The system 10 integrates location tracking solutions and data management solutions of alerts to create an interactive hierarchical overview of alerts. It correlates the physical distance between a device and an engineer with the alert data to provide a user-friendly overview. Among other features, the level of detail shown for each alert depends on the proximity to the engineer. For example, available service actions are displayed only for machines that are close to the engineer.

The medical devices are provided with a unique identifier by the physical location tracking mechanism. For example, a location tracking tag such as a smartcard could be attached to a device, such that the location of the smartcard determines the location of the device. The tag systemLocationUID is used to denote the identifier of the machine used in location tracking mechanism. The application can either collect and refresh this information regularly from a hospital database such as an install base inventory, or this data can be manually inserted and maintained.

Typically, each medical device is uniquely identified using some number and/or a string. For example, a device can be identified uniquely by their serial number while another device of a different modality could be uniquely identified by the combination of their system code (a number identifying the product model) and their serial number. The tag systemAlertUID is used to denote the identifier of a medical device as used in the alerting mechanism.

During the setup of the application, a one-to-one mapping is created between systemAlertUID and systemLocationUID. This results in a systemUID (being for example either systemAlertUID or systemLocationUID) that can be used to identify a medical device in both the alerting and location mechanisms, for example to perform the service action to medical device mapping operation 110 of FIG. 2.

In some embodiments, a user opens the app 42 in "setup mode" or "enroll new device mode". Here all new medical devices are connected to the alerting mechanism and to the location tracking mechanism. Otherwise, an error is returned in this step for the new device intended to be enrolled. The app 42 gets access to the alerting mechanism and downloads all systemAlertUIDs as well as all relevant metadata per device (AlertMetaData) that allows an end-user of the alerting mechanism to identify the device (e.g., an embodiment of operation 108 of FIG. 2). The following is an illustrative embodiment of the operation 110 of FIG. 2. The app 42 gets access to the location tracking mechanism and downloads all systemLocationUIDs as well as all relevant metadata per device (LocationMetaData) that allows an end-user of the location tracking mechanism to identify the device. The app 42 also can link AlertMetaData and LocationMetaData to make first guesses of matching identifiers using a scoring model. For example, SystemType and SystemSerialNumber tags can be used if present in both data sources as input for approximate string matching where the edit distance between two pairs defines its score. A user can then check and change each match if necessary. In addition, a user can scan a location tracking tag (e.g., QR code, RFID) for each device to make/change a match manually. That is, once a tag is scanned, it shows a list of potential candidates in the AlertMetaData ordered by their score. The user is asked to select the device that corresponds to the scanned tag.

The system 10 can also use a distance measurement of the location tracking system to calculate the distance between a user and the devices to determine the proximity of a user to the devices. Once a user is physically close to a device, the dashboard shows, in principle, alerts of that device only in the table T of FIG. 3. However, the dashboard can be configured to always show highly critical alerts that might require immediate action in the table T. The user opens the app 42 in 'scan device mode', and the software scans its environment for location tracking tags. If no tag is found the software asks the user to scan the tag attached to the device. Once the tag is scanned, the software selects the alerts that correspond to systemUID that is derived from the tag.

In some embodiments, the medical equipment are also assigned priorities, with the priority of each medical equipment 8 being based on the queued service actions for that medical equipment. For example, an item of medical equipment may be prioritized based on the highest severity of any service action in the queue for that medical equipment. Alternatively, an item of medical equipment may be prioritized based on some combination of the number and severities of the queued service action(s) for that medical equipment. As a nonlimiting illustrative example, a weighted sum can be used to assign a priority to an item of equipment, such as $P_n = \Sigma_{i=1}^N w(S_i) S_i$ where n denotes an item of medical equipment n, the index i=1, . . . , N indexes N queued service actions for medical equipment n, $S_i$ is the severity of queued service action i (where $S_i$ may, for example, assume values between 1 and 5 where 1 is least severe and 5 is highest severity), and $w(S_i)$ is a weight assigned to the severity $S_i$ (thus allowing for example to have $w(S_i=1)$ to be less than $w(S_i=5)$ to increase the contribution of higher priority queued service actions in the weighted sum. As previously noted, the N queued service actions contributing the priority $P_n$ may be limited to those queued service actions the user is qualified to perform. These are merely nonlimiting illustrative examples. In the map 30, the indicator 34 for each medical equipment 8 may indicate its priority $P_n$, for example by color coding based on its priority $P_n$ or labeling the medical equipment with is numerical priority $P_n$. This can help guide the user to medical equipment with highest priority, thereby improving overall performance of the user in efficiently handling maintenance tasks by guiding the user to the medical equipment with highest priority.

In a variant embodiment, the priority of each medical equipment may be adjusted based on distance, so as to assign higher priority to medical equipment that is closer to the current location of the user. Thus, for example, the priority could be $$P_n = \frac{K}{D} \sum_{i=1}^N w(S_i) S_i$$

where D is the distance from the user to the equipment n and K is a scaling constant. In this formulation of the priority, an item of medical equipment n at a larger distance D will have its priority $P_n$ reduced by the factor $$\frac{1}{D}.$$

This can neap guide me user to balance the overall severity of the queued service actions associated with a given medical equipment n with travel time to that medical equipment n, again improving overall performance of the user in efficiently handling maintenance tasks.

The app 42 also allows a user to select where some alerts are arisen in the hospital. In the setup phase, a digital map of the medical institution is created, where each location identifier of the location tracking mechanism is mapped to a point on the map. If the element is run on a device that is connected to the location tracking mechanism, e.g., a connected smartphone, it has its own location as potential input. A user can select a position, floor range, horizontal (i.e., floor distance) range, and alert density (i.e., low, medium, or high). on the app 42, and the user is shown a map of the area based on these selections. To set the input parameters, a user opens the software in normal mode. The user is shown a map of the room he/she is in with a red circle showing the amount of critical alerts. The user can drag the center point of the map and, thereby, change the parameter position. The user can zoom out and zoom in, thereby changing Horizontal-Range. The user can also type in values for all parameters.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium storing instructions executable by at least one electronic processor to perform a method of locating medical equipment to be serviced, the method comprising:
   accessing a map of a medical facility using an electronic processing device, the map including a plurality of medical equipment each having a tag indicative of a location thereof;
   determining what service tasks need to be performed for each of the plurality of medical equipment;
   determining which service tasks a user is qualified to perform;
   determining an assigned priority of the medical equipment;
   wherein the assigned priority is determined by $$P_n = \sum_{i=1}^N w(S_i) S_i;$$

modifying the map of the plurality of medical equipment to show only the medical equipment that include a service task the user can perform and the assigned priority of the medical equipment;

receiving a user input indicative of a selection of a medical equipment based on the modified display of the plurality of medical equipment; and displaying, on a display device of the electronic processing device, a list of service actions to be performed for the selected medical equipment and the map with an icon on the map indicating the user's proximity to the selected medical equipment.

2. The non-transitory computer readable medium of claim 1, wherein the method further comprises:

receiving a user input indicative of a selection of a portion of the map; and adjusting, on the display device, a display of the map.

3. The non-transitory computer readable medium of claim 2, wherein the adjusting comprises:

zooming in or zooming out of a selected portion of the map.

4. The non-transitory computer readable medium of claim 2, wherein the adjusting comprises:

showing a department or room on a selected portion of the map.

5. The non-transitory computer readable medium of claim 1, wherein the map includes queued service actions for the medical equipment, the queued service actions indicated by an indicator.

6. The non-transitory computer readable medium of claim 5, wherein the indicators are color-coded by severity.

7. The non-transitory computer readable medium of claim 5, wherein the method further includes:

determining qualifications of a user accessing the map using the electronic processing device; and showing the indicators for service actions for which the user is qualified to perform.

8. The non-transitory computer readable medium of claim 5, wherein the method further includes:

receiving a user input indicative of a selection of one of the indicators; and displaying information related to the service action corresponding to the selected indicator.

9. The non-transitory computer readable medium of claim 5, wherein the method further includes:

receiving a user input indicative of a selection of one of the indicators; and displaying information related to service actions corresponding to one or more indicators near the selected indicator.

10. The non-transitory computer readable medium of claim 1, wherein the method further includes:

determining a location of a user accessing the map using the electronic processing device;

receiving the user input indicative of a selection of a medical equipment;

displaying a path between the electronic processing device and the selected medical equipment.

11. The non-transitory computer readable medium of claim 10, wherein determining a location of a user accessing the map using the electronic processing device includes:

determining the location of the user using a real-time locating service (RTLS) dispersed throughout the medical facility.

12. The non-transitory computer readable medium of claim 10, wherein the RTLS includes tags attached to portable medical equipment.

13. The non-transitory computer readable medium of claim 10, wherein determining a location of a user accessing the map using the electronic processing device includes:

determining the location of the user using a tag affixed to the user.

14. The non-transitory computer readable medium of claim 1, wherein the method further includes:

retrieving, from a database, data indicative of queued service actions annotated to specific medical equipment; and generating indicators on the map indicative of the queued service actions.

15. The non-transitory computer readable medium of claim 14, wherein the method further includes:

retrieving, from the database, the data indicative of queued service actions annotated to specific medical equipment;

retrieving location data of the medical equipment; and matching the retrieved queued service action data to the location data to generate the indicators.

16. The non-transitory computer readable medium of claim 1, wherein the method further includes:

determining whether one or more medical equipment is unavailable for servicing; and marking indicators for unavailable medical equipment from the map.

17. The non-transitory computer readable medium of claim 1, wherein the method further includes:

determining priorities of the medical equipment having queued service actions based on the queued service actions for each medical equipment; and on the map, displaying indicators representing the determined priorities for the medical equipment having queued service actions.

18. The non-transitory computer readable medium of claim 17, wherein the indicators are determined further based on distances of the medical equipment from a location of a user.

19. A non-transitory computer readable medium storing instructions executable by at least one electronic processor to perform a method of locating medical equipment to be serviced, the method comprising:

accessing a map of a medical facility using an electronic processing device, the map including queued service actions for the medical equipment, the queued service actions indicated by indicators;

determining what service tasks need to be performed for each of the plurality of medical equipment;

determining which service tasks a user is qualified to perform;

determining an assigned priority of the medical equipment;

wherein the assigned priority is determined by $$P_n = \sum_{i=1}^{N} w(S_i) S_i;$$

modifying the map of the plurality of medical equipment to show only the medical equipment that include a service task the user can perform and the assigned priority of the medical equipment;

receiving a user input indicative of a selection of one of the indicators; and displaying information related to the service action corresponding to the selected indicator and the map with an icon on the map indicating the user's proximity to the selected medical equipment.

20. An apparatus, comprising:
a real-time locating service (RTLS) dispersed throughout a medical facility, the RTLS configured to determine locations of medical equipment in the medical facility;
and an electronic processing device programmed to:
access a map of the medical facility, the map including queued service actions for the medical equipment, the queued service actions indicated by an indicator;
determine what service tasks need to be performed for each of the plurality of medical equipment;
determine which service tasks a user is qualified to perform;
determine an assigned priority of the medical equipment;
wherein the assigned priority is determined by $$P_n = \sum_{i=1}^{N} w(S_i)S_i;$$

modify the map of the plurality of medical equipment to show only the medical equipment that include a service task the user can perform and the assigned priority of the medical equipment;
receive a user input indicative of a selection of a medical equipment of the plurality of medical equipment; and
display, on a display device of the electronic processing device, a list of service actions to be performed for the selected medical equipment and the map with an icon on the map indicating the user's proximity to the selected medical equipment.

* * * * *